(12) United States Patent
Lilly et al.

(10) Patent No.: US 6,548,245 B1
(45) Date of Patent: Apr. 15, 2003

(54) METHODS FOR DIAGNOSIS, PREDICTION AND TREATMENT OF ASTHMA AND OTHER INFLAMMATORY CONDITIONS BASED ON EOTAXIN CODING SEQUENCE POLYMORPHISM

(75) Inventors: Craig M. Lilly, Concord; Andrew D. Luster; Jeffrey M. Drazen, both of Winchester, all of MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/076,259

(22) Filed: May 12, 1998

Related U.S. Application Data (60) Provisional application No. 60/046,720, filed on May 16, 1997.

(51) Int. Cl.[7] ...................... A61K 39/395; C07H 21/04; C12Q 1/68; G01N 33/532; G01N 33/573

(52) U.S. Cl. ................... 435/6; 435/4; 435/7.1; 435/7.4; 536/22.1; 536/23.1; 536/24.3; 536/24.31; 424/139.1

(58) Field of Search .................... 435/4, 6, 7.1, 7.4; 424/139.1; 536/22.1, 23.1, 24.3, 24.31

(56) References Cited

PUBLICATIONS

W.F. Anderson, Human Gene Therapy, Nature 392, supplement, p. 25–30, Apr. 30, 1998.*

Abstract Only of "A Mutation in the Eotaxin Gene is Associated with the Asthma Phenotype," CM Lilly, et al., Journal of Respiratory and Critical Care Medicine, Apr. 1997.*

\* cited by examiner

*Primary Examiner*—David Guzo
*Assistant Examiner*—Jon Shuman
(74) *Attorney, Agent, or Firm*—Wolf, Greenfield and Sacks, P.C.

(57) ABSTRACT

Methods and compositions for diagnosing and treating asthma are provided. The methods involve the discovery of a correlation between an eotaxin gene polymorphism and the occurrence of asthma.

30 Claims, 2 Drawing Sheets

Wild Type Primers

FIG. 2A

Mutant Primers

FIG. 2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 4119 base pairs
      (B) TYPE: nucleic acid
      (C) STRANDEDNESS: single
      (D) TOPOLOGY: linear    (xi) SEQUENCE DESCRIPTION: SEQ ID NO:1:

```
AGGTTCTACA TTAGACTAAC CCACCGGGAA TGGAGCAGGA AGAACAGGG AAGACTCCAC      60

ATTTTTGGCC TCTATTTGGT AATTATAGTT AACTTTTTAG GTAATTATAG ACCAATTATC    120

CTAGATGGGC ACTTAGAGAC TTTGCAGGAC AGCAAGAGCT GTCTCTAATC CTGTGCCCAT    180

GACAGACATC ACCAGTCAAC CACAACACAG TATTTAACTA ACGCAAGTCA ACTCCTCAGA    240

ATCTTTAACA TTCTTGTTTG TGCTACTGTA CCAATCAATC AATTTGATAT GAGAGTGTGC    300

AGGAAAAAAC AGGAAACAGG TTTGCAGTAC CTCCACACCA GTATTCAATG CTGTAATCCG    360

CTGCAGTGAC TCCATTAAAG ACTTTGCCTC CCTTATACCC TCTCCAACTA GGGTGCCTAG    420

TGTTATGAAC AAAGGGATAT GTATAGGTTC TTGTGTTGCC TCTCTCTTTG ATATTTTTAG    480

CCATCAGATA CCTTGTCTGC AATGTGTGCT CAGAGAGTGA GGGGGGAACT AGATGATTGA    540

TTTTCCAAAT GTGTTCCCTA AATGTGTTCC CTGGGGAATA AGGGCACGAG AGGCTGCCTA    600

TTCTATTTCA AACAAATCCC CTTCACTACA GTGTATTTGA TGAGTTGGGG TTTGTTTTAA    660

TTCCATTTGG AAAAGGGCTT TAGCAGCTAA GCAAATGGTT TTAAAGTGCC TCAGAAGTCA    720

AGATTAATAG AAACTATCCA GTTCTGATGT CCTATCATGC TAAAATTTCA GGGACTAAGA    780

TTCTGTGATC ATTACATTGA AACACAGCAG CAAAGCTGTG GTGTGTTGTC CTTCCTGGTT    840

CAGAGATGCA ACTATGTGCA GGGCTGCTGA GCTCTCTCTG CATCTGGGTG GGAGCCTAAT    900

GGAAGTTTTG GGGCTCCTTC CTGGTCTCCA AAATCCTCAA GACCACCATG TGAACACAGG    960

AATCAAGGAA GGTTCTTAGA TCGACTCATC CCCCAGGCCT TTGGTTTCCT TGCTCTTTTC   1020

CCCAACTACA GGTGTTTCAT TTCAACTCAT CCCCTAGGGC CTTGGTTTTC TTGCTCTCTT   1080

CCCCCACTAC AGATGTTTAA CTTCATTTCA TAACCACATA TTCCCCTCCT TTTCCAAGGC   1140

AAGATCCAGA TGGATTAAAA AATGTACCAA GTCCCTCCTA CTAGCTTGCC TCTCTTCTGT   1200

TCTGCTTGAC TTCCTAGGAT CTGGAATCTG GTCAGCAATC AGGAATCCCT TCATCGTGAC   1260

CCCCGCATGG GCAAAGGCTT CCCTGGAATC TCCCACACTG TCTGCTCCCT ATAAAAGGCA   1320

GGCAGATGGG CCAGAGGAGC AGAGAGGCTG AGACCAACCC AGAAACCACC ACCTCTCACG   1380
```

-continued

```
CCAAAGCTCA CACCTTCAGC CTCCAACATG AAGGTCTCCG CAGCACTTCT GTGGCTGCTG    1440

CTCATAGCAG CTGCCTTCAG CCCCCAGGGG CTCGCTGGGC CAGGTAAGCC CCCCAACTCC    1500

TTACAGGAAA GGTAAGGTAA CCACCTCCAG AGCTACTAGG TCAGCAAGAA TCTTTACAGA    1560

CTCACTGCAA ATTCTCCATT TGAAAAATAG GGAAACAGGT TTTGTGGGTG ACAAGAAAT     1620

GCCTCAACCT CACATCCAGT CACTGGAAGA GCCAGAACTA GAAAGCTCCC GAGTCTTTTC    1680

CCCACATTCA AGAGGGCCGC TGGGTGCATC CTTACCCAGC TATCCTTACA GTGTTTGGGA    1740

ATGGGGAATG GCTCTGTCTT ACTGTGGGCA TGGTGGGCAT TTTTGGCAGT GGGAGAGAAG    1800

GAAAATCTGT TGATTAGAAG CTCAGTATGT TAATTCGACT CCAGGACAGC TTTCAGAGAC    1860

AGTGGCTAAG AGAAGAACGA GGTCCCAGGG GATCTCTTGA GGTGACTTAT TTTGACACTC    1920

TTTGGGAAAG TTATCTAGGA GATTTGTTCC ATAACTCATT TTCCCATACT CTGGTGACAA    1980

ATTTACTGAG TGTATCGGTC CCACTGAGCC AGTGCATAGC ATGGTAACAA ACAGTTCTAA    2040

ATTATCAATG ACTTAACAGA ATTAACTAAA TTAACAAAAG TTACTTTCTC ACTTGTACTA    2100

AATATCTATA ATGTATGGGC TCAGGCTTCT GCATTTTATA CTCAGGATTC TAGACTGATG    2160

GAGAAGTTGC CATGTGGGGG AACATTGATG GATACTGTGA TAAAGCAGAA GAAAGCTCTC    2220

AGGAGTCTTG CATAGGCAAT GCACTGTGGC TCAAAAATGA CACCCATCAC TTTGTCTCCT    2280

TCTTTATTGA TCAAAACTAA TTAATGCCTC CAACCAAACA AAAGTGGCCA AGAAATGCAA    2340

GTCTACCTTG TGTCTCAAAA CAGAGGATGG AGAATATTTG GTGAAAATTA CCATGACCAT    2400

CACATGGCCA CGTAGGTCTT TATAATGACA GAGCTAGCAT TTGTCACATT GACCAAGCTT    2460

TGTCCATACA CTCTACAGTA ATGATGAGTC CTCAGTGCAC AGGGGAGGAT GCTGAAGACA    2520

CAGGACAGCA TCCTCCAGAC ACATAAGACT TCAGAGCAGA GGGATTCTCC CTCCACCTCT    2580

CGCAATTCCT TGCTTTCTCC TAACTTCCTT TACAAAGTCA TGCTTGGAAA TGTCTATGTA    2640

TCATCATGTG GCTCATTTTT TTCTCTGTTC ATTTTTTTTC CCCAAAATTC AGCTTCTGTC    2700

CCAACCACCT GCTGCTTTAA CCTGGCCAAT AGGAAGATAC CCCTTCAGCG ACTAGAGAGC    2760

TACAGGAGAA TCACCAGTGG CAAATGTCCC CAGAAAGCTG TGATGTAAGT AAATAAAGTT    2820

CACCCTCCCC TAGACAAAAA AATAATGTCT AGGGCACAGA GTCAAGAACT GTGGGAGTCA    2880

TAGACTCTGA TAGTTTGACC TCTATGGTCC AATTCATTAA TTTTCACAAG TGAGTGTTCA    2940

CTCCCAGCTC CCTGCCTGGG AGATTGCTGT AGTCATATCA ATTTCTTCAA GTCAAGAGCA    3000

AAGATGGTTT TACTGGGCCT TTAAGAGCAG CAACTAACCC AAGAGTCTCA TCCTTCCTCC    3060

TCTCCGTAGC AACCCTTTGT CCAGGGGCAG ATGGTCCTTA AATATTTAGG GTCAAATGGG    3120

CAGAATTTTC AAAAACAATC CTTCCAATTG CATCCTGATT CTCCCCACAG CTTCAAGACC    3180

AAACTGGCCA AGGATATCTG TGCCGACCCC AAGAAGAAGT GGGTGCAGGA TTCCATGAAG    3240

TATCTGGACC AAAAATCTCC AACTCCAAAG CCATAAATAA TCACCATTTT TGAAACCAAA    3300

CCAGAGCCTG AGTGTTGCCT AATTTGTTTT CCCTTCTTAC AATGCATTCT GAGGTAACCT    3360

CATTATCAGT CCAAAGGGCA TGGGTTTTAT TATATATATA TATATATATT TTTTTTAAA    3420

AAAAAACGTA TTGCATTTAA TTTATTGAGG CTTTAAAACT TATCCTCCAT GAATATCAGT    3480

TATTTTTAAA CTGTAAAGCT TTGTGCAGAT TCTTTACCCC CTGGGAGCCC CAATTCGATC    3540

CCCTGTCACG TGTGGGCAAT GTTCCCCCTC TCCTCTCTTC CTCCCTGGAA TCTTGTAAAG    3600

GTCCTGGCAA AGATGATCAG TATGAAAATG TCATTGTTCT TGTGAACCCA AAGTGTGACT    3660

CATTAAATGG AAGTAATGTT GTTTTAGGAA TACATAAAGT ATGTGCATAT TTTATTATAG    3720

TCACTAGTTG TAATTTTTTT GTGGGAAATC CACACTGAGC TGAGGGGGAC AAAGATGGCT    3780
```

```
GTGGCCAAGA GGGGCTTGGT TAAGGGGGTG GGAACTATGT CCCTGGGAAA TGAGTTTTTG    3840

GCTTAGCTGG TCTTCATTGA AATGCAGGGT GAAACTGACA AACCCATTCC AGCCCTCTAT    3900

TCCCATTTTC AACAGTATTT CCCAGACCCC AAACTTCAGC CACGAAAATA TCTGGAGCTT    3960

TGCCACCATT CCTTTCCTCC CCACCTCATA CTTGCCTCTC CTGGGACCTA TTTTAACAGC    4020

CCTGTGGTAT CTCCCTCTAC CCGACCCTGC TCCTCGGTCT TCCAACCCAG ACTAGGCAGA    4080

CATGACAGAC ACTGGAAATC AGAGGAAGGC TAGGTGACC                           4119
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: Other     (xi) SEQUENCE DESCRIPTION: SEQ ID NO:2:

```
AGAAACCACC ACCTCTCACG                                                  20
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: Other     (xi) SEQUENCE DESCRIPTION: SEQ ID NO:3:

```
GAGAATTTGC AGTGAGTCTG T                                                21
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (ii) MOLECULE TYPE: Other     (xi) SEQUENCE DESCRIPTION: SEQ ID NO:4:

```
GGGGCTTACC TGGCCCAAC                                                   19
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (ii) MOLECULE TYPE: Other     (xi) SEQUENCE DESCRIPTION: SEQ ID NO:5:

```
GGGGCTTACC TGGCCCAAT                                                   19
```

(2) INFORMATION FOR SEQ ID NO:6:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: Other (xi) SEQUENCE DESCRIPTION: SEQ ID NO:6:

TCAAGGAAGG TTCTTAGATC G                                                   21
```

METHODS FOR DIAGNOSIS, PREDICTION AND TREATMENT OF ASTHMA AND OTHER INFLAMMATORY CONDITIONS BASED ON EOTAXIN CODING SEQUENCE POLYMORPHISM

RELATED APPLICATIONS

This application claims priority under Title 35, United States Code, §119(e), of U.S. Provisional application Ser. No. 60/046,720, filed May 16, 1997, and entitled "Methods for Diagnosis, Prediction and Treatment of Asthma and Other Inflammatory Conditions Basedron Eotaxin Coding Sequence Polymorphism", the entire contents of which are incorporated herein by reference.

This invention resulted from research sponsored, in part, by NIH Grant Number HL0328. The Government has certain rights in this invention.

BACKGROUND OF THE INVENTION

This invention pertains to disease diagnosis, prediction and treatment and, more particularly, to diagnosis, prediction and treatment of asthma, rhinitis and other inflammatory conditions associated with eosinophil accumulation in respiratory and other tissues.

Asthma is a respiratory ailment characterized by airway obstruction, inflammation and/or hyperresponsiveness. According to a 1994 survey by the U.S. Department of Health and Human Services, over 12 million Americans suffer from asthma, almost 5 million of them under the age 18. Long-term medications include corticosteroid, beta-agonists and leukotriene modifiers. For quick relief, anticholinergics, corticosteroids, and/or beta-agonists may be applied. Adverse side effects of these treatments include cough, dysphonia, candidiasis (corticosteroids), tachycardia, muscle tremor, hypokalemia, hyperglycemia (beta-agonists), liver impairment (leukotriene modifiers), drying of mouth and respiratory secretions (anticholinergics).

The standard of care for asthma dictates that treatment with the foregoing medications be a guided by disease severity of the symptoms. Since the nature of asthma is to have exacerbations and remissions, this approach undertreats patients with the potential to develop significant airway inflammation, but who at the time of pulmonary function testing are in a physiological remission. In addition, this approach can result in application of medications of greater toxicity then truly required for the condition.

One characteristic of inflammatory reactions, such as asthma and rhinitis, is the accumulation of eosinophils in the mucosal lining of the affected organs. Recruitment of eosinophils is thought to be mediated by a class of proteins known as chemokines and, particularly, by the protein eotaxin. That ligand is understood to have a high affinity for so-called CC-CKR3 receptors, which are found in large numbers on the surfaces of eosinophils.

In view of the foregoing, an object of this invention use to provide improved compounds and methods for prediction, diagnosis and treatment of disease and, more particularly, improved compounds and methods for prediction, diagnosis and treatment of asthma, rhinitis and other inflammatory conditions of respiratory and other tissues.

A further object of the invention is to provide such improved compounds and methods as permit control of such inflammatory conditions without undue risk of under- or over-treatment.

Yet another object of the invention is to provide such improved compounds and methods as permit prediction, diagnosis and treatment of such inflammatory conditions in a cost effective manner.

SUMMARY OF THE INVENTION

The foregoing objects are among those attained by the invention, which facilitates prediction, diagnosis and treatment of inflammatory conditions through exploitation of a heretofore unknown association between those conditions and a polymorphism of the eotaxin gene.

Thus, for example, the invention provides a method for diagnosis of asthma based on identification a substitution of adenine for guanine 67 base pairs following the ATG initiation codon (initiating counting at the A in that codon) of the eotaxin gene or, alternatively, based on identification of a substitution of threonine for alanine in the 23rd position of the resulting protein. The wild type (normal) eotaxin gene (i.e., without the aforementioned polymorphic substitution) is shown as SEQ ID NO: 1, below.

In a related aspect, the invention provides methods for prediction or diagnosis of asthma or other inflammatory conditions associated with tissue accumulation of eosinophils, such rhinitis and atopy, based on diagnosis of the foregoing substitutions.

Further aspects of the invention provide methods as described above in which the adenine/guanine substitution is identified by analysis of DNA or MRNA (or on other nucleic acid sequences, such as cDNA, developed therefrom) in tissue, blood or other biological samples taken from a patient or kindred thereof. Such analysis can include sequencing or probing those sequences using otherwise known techniques, as adapted to identify the aforementioned polymorphism.

In one preferred aspect of the invention, the nucleotide sequences in the samples are amplified, e.g., via polymerase chain reaction (PCR), and the amplified product is analyzed for evidence of the substitution. Such amplification can be performed, e.g., using conventional PCR or, preferably, using single-strand conformation polymorphism (SSCP) and/or amplification refractory mutation system (ARMS) techniques, though other amplification techniques known in the art can be used as well.

Further aspects of the invention provide methods as described above in which the threonine/alanine substitution is identified by contacting the biological samples with immunolabelling agents, such as monoclonal or polyclonal antibodies, raised against the variant protein (i.e., the protein resulting from the eotaxin gene with the aforementioned adenine/guanine substitution).

Still other aspects of the invention provide novel chemical compounds, notably, nucleic acid sequences for use in the diagnosis, prediction and/or treatment of the aforementioned inflammatory conditions.

BRIEF DESCRIPTION OF THE DRAWINGS

A more complete understanding of the invention may be attained by reference to the drawings, in which.

DESCRIPTION OF THE SEQUENCES

SEQ ID NO: 1 is the wild type (normal) sequence for the human eotaxin gene;

SEQ ID NO: 2 and SEQ ID NO: 3 are oligonucleotide sequences used in one practice of the invention as primers for PCR and/or SSCP analysis of nucleotide sequences; and SEQ ID NO: 4, SEQ ID NO: 5 and SEQ ID NO: 6 are oligonucleotide sequences used in one practice of the invention as primers for ARMS analysis of nucleotide sequences.

DETAILED DESCRIPTION OF THE ILLUSTRATED EMBODIMENT

A genetic contribution to the pathogenesis of asthma has long been inferred from the increased prevalence of asthma in families. The association of genetic markers with airway hyperresponsiveness, a defining physiological feature of asthma, in affected kindreds implies that genetic factors can influence asthma pathogenesis (1)*. That specific genetic polymorphisms are associated with the asthma phenotype is supported by a growing number of association studies. Many of these studies have been undertaken because there is reason to believe that the target genes are relevant to pathogenesis or severity of allergic diseases including asthma (2). For example it is now known that differences in the post stimulation presence of the beta-adrenergic receptor on isolated cells in vivo are related to polymorphic variants of the beta-adrenergic receptor gene (3–5) and that the occurrence of one polymorphic form of the $\beta_2$ adrenergic receptor ($\beta_2$AR) is associated with airway hyperresponsiveness in vivo. Further, this polymorphism has been associated with the nocturnal and steroid requiring form of asthma (6,7). The relevance of genetic polymorphisms to asthma is further supported by the association of polymorphisms in the 5-lipoxygenase gene (8), and the IL-4 gene (9,10) with the asthma phenotype. Awareness and analysis of asthma relevant genetic polymorphisms has the potential to allow the development of treatment strategies that are guided by genetic analysis.

*Numeric expressions in parenthesis refer to publications and other disclosures listed in the endnotes, the teachings of which are incorporated herein by reference.

It is now widely recognized that asthma is a disease of airway inflammation and that eosinophils and their products are present in the airways of mild as well as severe asthmatics (11–14). The airway presence of eosinophils may be important in asthma because eosinophil products can disrupt airway function (15–17). Interestingly, therapeutic responses to asthma treatment are associated with a decrement in the presence of eosinophils and their products (18–20). The recent discovery of the CCK-3 receptor on eosinophils and its specific ligand eotaxin has defined a novel mechanism by which eosinophils can be recruited into the airways (21–23). associated eotaxin with the presence of eosinophils (24).

Based on these associations and the identification of eotaxin cDNA sequence variants in a mixed population of dermal fibroblasts (25), we have discovered a polymorphism in the coding region of the eotaxin gene that correlates with the incidence of asthma. The wild type (normal) eotaxin gene is shown below as SEQ ID NO: 1. The polymorphism that we have discovered comprises substitution of adenine for guanine 67 base pairs following the ATG initiation codon (initiating counting at the A in that codon) of the gene. The variant eotaxin protein produced by that polymorphism incorporates the amino acid threonine in its 23rd position, in lieu of the amino acid alanine that occupies that position in the normal eotaxin protein.

One embodiment of our invention comprises detecting asthma by identifying this polymorphism in DNA or mRNA (or on other nucleic acid sequences, such as cDNA, developed therefrom) contained in tissue, blood or other biological samples taken from a patient. The polymorphism can be detected in any manner conventionally known in the art, e.g., via directly sequencing the nucleotide sequences contained in the samples, though it is preferably detected by, first, amplifying those sequences, e.g., via polymerase chain reaction (PCR).

Alternatively, or in addition, the disease can be detected by identification of the variant protein in those tissues. Such diagnosis or even prediction can also be made by identifying the polymorphism or variant protein in samples taken from kindred or other relatives of a human being. This can be helpful, for example, in determining whether offspring are likely to be genetically predisposed to the condition, even though it has not expressed itself in the parents.

In one preferred embodiment of the invention, amplification and detection is using single-strand conformation polymorphism (SSCP) and/or amplification refractory mutation system (ARMS) techniques, though other amplification techniques known in the art can be used as well.

Where conventional PCR or SSCP are used, preferred primers include the oligonucleotides AGAAACCACCACCTCTCACG (SEQ ID NO: 2) and

GAGAATTTGCAGTGAGTCTGT (SEQ ID NO: 3)

or functional equivalents thereof. Where the ARMS technique is used, the forward primers can include GGGGCTTACCTGGCCCAAC (SEQ ID NO: 4) and

GGGGCTTACCTGGCCCAAT (SEQ ID NO: 5)

or functional equivalents thereof The reverse primer for the ARMS technique can include

TCAAGGAAGGTTCTTAGATCG (SEQ ID NO: 6)

or functional equivalents thereof.

In further embodiments, the invention provides for treatment of asthma by detecting and remediating (e.g., via conventional gene therapy techniques) the genomic polymorphism either systemically or in the affected tissues. Alternatively, such treatment may be attained through detection of the polymorphism or variant protein, and by application of appropriate medications, e.g., for blocking the CCK-3 receptor.

In addition to asthma, the invention can be applied to the diagnosis, prediction and/or treatment of rhinitis, atopy, and other inflammatory diseases associated with accumulation of eosinophils in the mucus or tissues. The foregoing techniques can likewise be applied to other mammals that synthesize, utilize and/or metabolize eotaxin in a manner similar to that of humans.

EXAMPLE

Detection of Eotaxin Polymorphisms in Patients Suffering from Asthma

Patient Materials: The American Thoracic Society criteria for the diagnosis of asthma were met in 128 subjects who had disease of varying severity. Normal subjects were defined by the absence of detected medical disease and a negative history for asthma and atopy. In addition, each of the 81 normal subjects failed to react to the intra-dermal injection of 12 common aero-allergens. The source of DNA for single-strand conformation polymorphism (SSCP) analysis was a lymphocyte density gradient enriched fraction of fresh whole blood that was immortalized using a standard Epstein Barr virus protocol (26,27). These cells were obtained from 25 normal subjects and 25 subjects with asthma treated only with inhaled beta-agonists. For the amplification refractory mutation system (ARMS) technique, additional DNA was harvested from the whole blood of 35 mild asthmatics, 28 subjects with near fatal asthma, one subject with fatal asthma and 56 normal subjects. DNA was isolated by buccal brushing from an additional 39 subjects with steroid requiring asthma. DNA was extracted using a commercially available kit according to the instructions of the manufacturer (Stratagene, La Jolla, Calif.).

PCR: Twenty and 21 base oligomers were synthesized using an Abacus DNA synthesizer. The sequence of these oligimers was AGAAACCACCACCTCTCACG (SEQ ID NO: 2) and GAGAATTTGCAGTGAGTCTGT (SEQ ID NO: 3) respectively. PCR was performed using 20 μl reaction volumes containing 10 mM Tris•HCl, 50 mM KCl, 0.1 μl genomic DNA, a primer concentration of 2 μM, and 2.5 mM MgCl$_2$ and covered with oil. The reaction mixture was denatured at 95° C. for 5 min and placed at 80° C. All four dNTPs were added to a final concentration of 0.2 mM including 1.25 μCi of (P)dATP. After the addition of 2.5 units of AmpliTaq DNA polymerase (Perkin-Elmer/Cetus) 25 cycles of PCR were preformed with a 2 minute 55° C. annealing segment followed by a 3 minute 72° C. extension segment and a 1 minute 94° C. denaturation segment. a 7 minute 72° C. extension segment followed the final cycle.

SSCP: SSCP was performed by the method of Beier (28). Briefly, the PCR solution was diluted 1.5:10 in a stop solution of 100% formamide containing xylene cyanol and bromophenol blue, denatured for 5 minutes at 94° C. and placed on ice. a 4 μl sample was loaded on to an MDE gel (AT Biochem, Malvern Pa.) and subjected to a 5 to 6 hour electrophoresis at 4° C. in 0.6×TBE at 60W constant power. The PCR products were transferred from the gel to filter paper, dried, and subjected to autoradiography overnight with an intensifying screen.

ARMS: The presence or absence of a 530 bp band was determined for paired PCR reactions under the following conditions. The sequences of the forward primers were GGGCTTACCTGGCCCAAC (SEQ ID NO: 4) and GGGGCTTACCTGQCCCAAT (SEQ ID NO: 5) respectively and the sequence of the reverse primer was TCAAG-GAAGGTTCTTAGATCG (SEQ ID NO: 6). Each 20 μl reaction contained 0.1 μg of DNA, 2.0 mM MgCl$_2$, a 0.2 mM dNTP mixture, and 0.5 μM primers. Each reaction was subjected to the following amplification procedure: denaturation at 94° C. for 5 minutes, addition of 2.0 units of AmpliTaq DNA polymerase, annealing at 56° C. for 30 seconds, extension at 72° C. for 1 minute, and denaturation at 94° C. for 40 seconds. Thirty amplification cycles were followed by a 5 minute 72° C. segment extension period. The electrophoretic mobility of the reaction products was determined on a 2% agarose gel. The ARMS band detection pattern corresponded to the sequence and SSCP determined genotype for each of the 50 samples studied.

DNA Sequencing: The eotaxin DNA sequence of each of the 25 asthmatic and 25 normal subjects was determined by cycle sequencing PCR generated fragments from these subjects. PCR was performed for 20 cycles as described above but using non-radiolabeled dATP. Cycle sequencing was performed using a commercially available kit according to the instructions of the manufacturer (Life Technologies, Gaithersburg, Md.).

Results

Figure 1A:
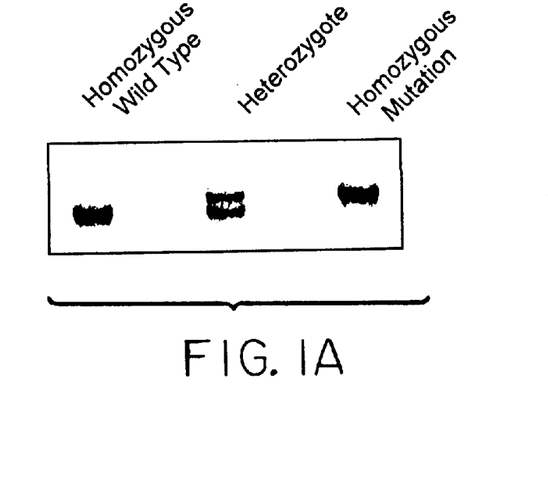
FIG. 1A depicts a portion of an electrophoretic pattern resulting from SSCP analysis of lymphocyte density gradient enriched fractions of fresh whole blood from normal and asthmatic patients.
Figure 1B:
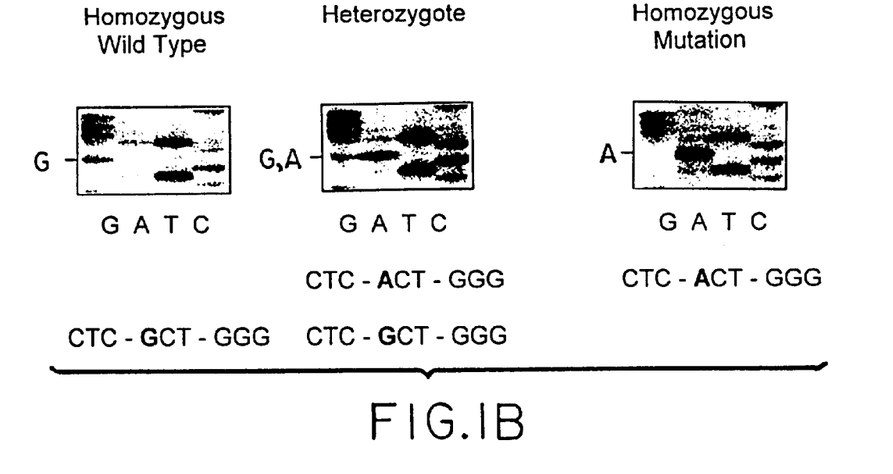
FIG. 1B depicts a portion of an electrophoretic pattern resulting from di-deoxy DNA sequencing of DNA from normal and asthmatic patients.
Figure 1C:
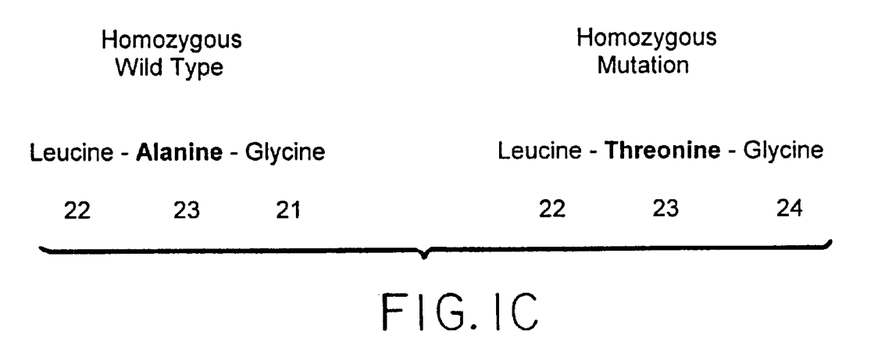
FIG. 1C depicts the threonine/alanine substitution in the eotaxin protein sequence resulting from the adenosine/guanidine in the eotaxin gene.

SSCP analysis demonstrated three distinct electrophoretic patterns presented in FIG. 1A. a single distinct band was noted in lanes corresponding to 18 of the normal subjects and 2 bands were noted in 7 of these subjects. A single band with the same electrophoretic mobility of the single band noted in normal subjects was present in 15 of the lanes corresponding to asthmatic subjects. Seven lanes from asthmatic subjects demonstrated 2 bands and 3 lanes had a single band with different electrophoretic mobility. Di-deoxy DNA sequencing of the relevant DNA from each of these 50 subjects revealed 3 distinct sequence patterns that corresponded exactly with the SSCP patterns. a single base pair substitution polymorphism was detected 67 base pairs in the 3' direction from the ATG initiation codon of the eotaxin gene, FIG. 1B. This polymorphism would alter the predicted eotaxin protein sequence by replacing the alanine at position 23 with the polar amino acid threonine (C). The normal subjects all had at least one allele containing a guanidine residue. This sequence is the known eotaxin sequence. Three of the asthmatic subjects were homozygous for a variant form of eotaxin that had an adenosine residue at this locus.

Figure 2A:
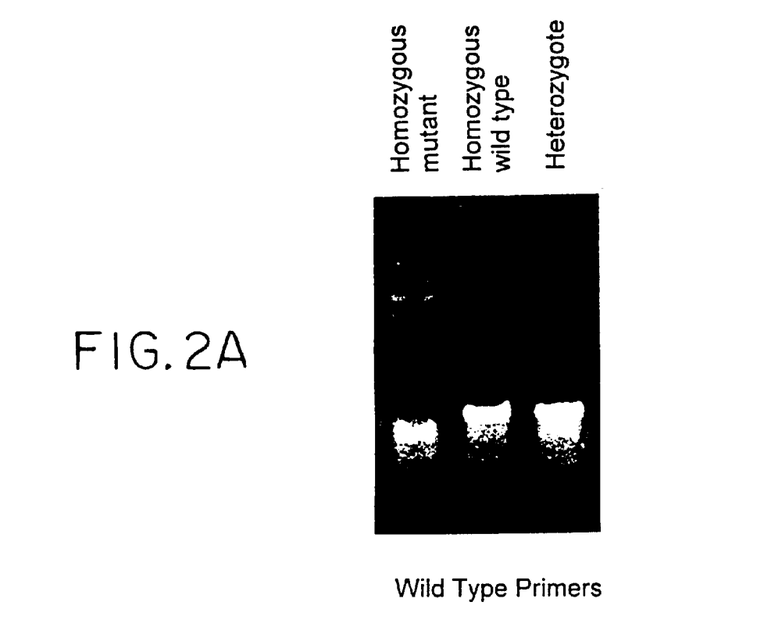
FIGS. 2A–B depicts a representative set of gels demonstrating the presence or absence of a 530 bp PCR product from pairs of reactions.
Figure 2B:
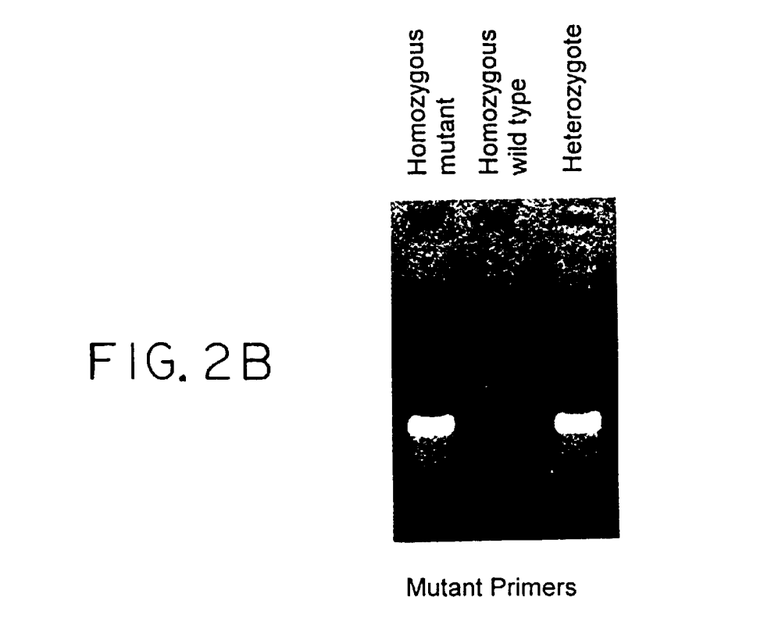

Using the ARMS technique we determined the frequency of the homozygous form of this polymorphism in 128 asthmatic subjects and 81 normals. We found that a significantly higher frequency of this polymorphism in asthmatic compared to normal subjects, Table I ($\chi^2$, p<0.05). a representative set of gels demonstrating the presence or absence of a 530 bp PCR product from pairs of reactions is presented in FIG. 2.

|  | Homozygous Mutant | Non-Homozygous Mutant |
| --- | --- | --- |
| Normals | 0 | 81 |
| Asthmatics | 6 | 128 |

Discussion

We have detected a polymorphism in the eotaxin gene at a position that alters the predicted sequence of the translated protein product at a locus near the site where the "leader" sequence is removed. This finding is in accord with the detection of an eotaxin variant in a mixed population of dermal fibroblasts (25). In contrast to that report, our finding that different forms of the eotaxin gene are present in different individuals establishes the existence of this eotaxin polymorphism and its higher frequency of its homozygous form in patients with asthma.

This codon 69 single base pair substitution of an adenosine for a guanidine residue 67 base pairs after the ATG initiation codon alters the predicted protein sequence of eotaxin by substituting the polar amino acid threonine for the hydrophobic amino acid alanine. This alteration occurs at human eotaxin amino acid position 23. The presence of this sequence alteration near the terminus of the hydrophobic leader sequence suggests that it may alter the rate or pattern of eotaxin processing relative to its secretion.

The potential biological role of eotaxin for recruiting eosinophils to the airways after allergic stimulation (21,23, 24,29) similar to that which occurs in asthma suggested that altered forms of eotaxin may be relevant to asthma. We therefore compared the frequency of the polymorphism in well characterized asthmatics to that of non-atopic normals. We found that 30% of our population of non-atopic normals and 25% of our asthmatics are heterozygous for this polymorphism. Interestingly 5% of our asthmatic population was homozygous for this polymorphism while we did not detect any homozygotes in our population of normals. We did not observe, but were unlikely to detect, any association of this polymorphism with asthma severity.

The effect of the presence of this polymorphism on eosinophil biology remains incompletely investigated. We have observed increased numbers of eosinophils in the peripheral blood of asthmatic subjects that are homozygous for this polymorphism suggesting that it may enhance eosinophil recruitment into the blood or prolong eosinophil survival. Alternatively, the lack of the wild type form of eotaxin may inhibit the egress of eosinophils from the blood into the tissues.

In summary, we have discovered that a polymorphism in the eotaxin gene and resultant variant in the eotaxin protein that can be exploited for purposes of diagnosis, prediction and treatment of asthma, rhinitis and other inflammatory conditions.

The list of references is presented below and is followed by the Sequence Listing and What is Claimed:

REFERENCES CITED AND INCORPORATED HEREIN BY REFERENCE

1. Postma, D. S., E. R. Bleecker, P. J. Amelung, K. J. Holroyd, J. Xu, C. I. Panhuysen, D. A. Meyers, and R. C. Levitt. 1995. Genetic susceptibility to asthma—bronchial hyperresponsiveness coinherited with a major gene for atopy. *N. Engl. J. Med.* 333:894–900.
2. Sandford, A. J., T. Shirakawa, M. F. Moffatt, S. E. Daniels, C. Ra, J. A. Faux, R. P. Young, Y. Nakamura, G. M. Lathrop, and W. O. Cookson. 1993. Localisation of atopy and beta subunit of high-affinity IgE receptor (Fc epsilon RI) on chromosome 11 q. *Lancet* 341:332–334.
3. Green, S. A., J. Turki, M. Innis, and S. B. Liggett. 1994. Amino-terminal polymorphisms of the human beta 2-adrenergic receptor impart distinct agonist-promoted regulatory properties [published erratum appears in Biochemistry 1994 Nov 29;33(47): 14368. *Biochemistry* 33:9414–9419.
4. Green, S. A., J. Turki, P. Bejarano, I. P. Hall, and S. B. Liggett. 1995. Influence of beta 2-adrenergic receptor genotypes on signal transduction in human airway smooth muscle cells. *Am. J. Respir. Cell Mol. Biol.* 13:25–33.
5. Hall, I. P., A. Wheatley, P. Wilding, and S. B. Ligett. 1995. Association of Glu 27 beta 2-adrenoceptor polymorphism with lower airway reactivity in asthmatic subjects. *Lancet* 345:1213–1214.
6. Szefler, S. J., R. Ando, L. C. Cicutto, W. Surs, M. R. Hill, and R. J. Martin. 1991. Plasma histamine, epinephrine, cortisol, and leukocyte beta-adrenergic receptors in nocturnal asthma. *Clin. Pharmacol. Ther.* 49:59–68.
7. Turki, J., J. Pak, S. A. Green, R. J. Martin, and S. B. Liggett. 1995. Genetic polymorphisms of the beta 2-adrenergic receptor in nocturnal and nonnocturnal asthma. Evidence that Gly16 correlates with the nocturnal phenotype. *J. Clin. Invest.* 95:1635–1641.
8. In, K. H., K. Asano, D. Beier, J. Grobholz, P. W. Finn, E. K. Silverman, E. S. Silverman, T. Collins, A. R. Fischer, T. P. Keith, K. Serino, S. W. Kim, G. T. De Sanctis, C. Yandava, P. Rubin, J. Kemp, E. Israel, W. Busse, D. Bedford, J. J. Murray, A. Segal, D. Tinkleman, and J. M. Drazen. 1997. Naturally occurring mutations in the human 5-lipoxygenase gene promoter which modify transcription factor binding and reporter gene transcription. *J. Clin. Invest.* (in press).
9. Borish, L., J. J. Mascali, M. Klinnert, M. Leppert, and L. J. Rosenwasser. 1995. SSC polymorphisms in interleukin genes. *Hum. Mol. Genet.* 4:974
10. Rosenwasser, L. J., D. J. Klenim, J. K. Dresback, H. Inamura, J. J. Mascali, M. Klinnert, and L. Borish. 1995. Promoter polymorphisms in the chromosome 5 gene cluster in asthma and atopy. *Clin. Exp. Allergy* 25 Suppl 2:74–8.
11. Dunnill M. S. 1960. The pathology of asthma, with special reference to changes in the bronchial mucosa. *J. Clin. Pathol.* 13:27–33.
12. Bousquet, J., P. Chanez, J. Y. Lacoste, G. Barneon, N. Ghavanian, 1. Enander, P. Venge, S. Ahlstedt, J. Simony-Lafontaine, P. Godard, and et al. 1990. Eosinophilic inflammation in asthma. *N. Engl. J Med.* 323:1033–1039.
13. Broide, D. H., G. J. Gleich, A. J. Cuomo, D. A. Coburn, E. C. Federman, L. B. Schwartz, and S. I. Wasserman. 1991. Evidence of ongoing mast cell and eosinophil degranulation in symptomatic asthma airway. *J. Allerg. Clin. ImmunoL* 88:637–648.
14. Wardlaw, A. J., S. Dunnette, G. J. Gleich, J. V. Collins, and A. B. Kay. 1988. Eosinophils and mast cells in bronchoalveolar lavage in subjects with mild asthma. Relationship to bronchial hyperreactivity. *Am. Rev. Respir. Dis.* 137:62–69.
15. Uchida, D. A., S. J. Ackerman, A. J. Coyle, G. L. Larsen, P. F. Weller, J. Freed, and C. G. Irvin. 1993. The effect of human eosinophil granule major basic protein on airway responsiveness in the rat in vivo. A comparison with polycations. *Am. Rev. Respir. Dis.* 147:982–988.
16. Hisamatsu, K., T. Ganbo, T. Nakazawa, Y. Murakami, G. J. Gleich, K. Makiyama, and H. Koyama. 1990. Cytotoxicity of human eosinophil granule major basic protein to human nasal sinus mucosa in vitro. *J. Allergy Clin. Immunol.* 86:52–63.
17. Ayars, G. H., L. C. Altman, M. M. McManus, J. M. Agosti, C. Baker, D. L. Luchtel, D. A. Loegering, and G. J. Gleich. 1989. Injurious effect of the eosinophil peroxide-hydrogen peroxide-halide system and major basic protein on human nasal epithelium in vitro. *Am. Rev. Respir. Dis.* 140:125–131.
18. Laitinen, L. A., A. Laitinen, and T. Haahtela. 1992. A comparative study of the effects of an inhaled corticosteroid, budesonide, and a beta 2-agonist, terbutaline, on airway inflammation in newly diagnosed asthma: a randomized, double-blind, parallel-group controlled trial. *J Allergy Clin. Immunol.* 90:32–42.
19. Burke, C., C. K. Power, A. Norris, A. Condez, B. Schmekel, and L. W. Poulter. 1992. Lung function and immunopathological changes after inhaled corticosteroid therapy in asthma. *Eur. Respir. J.* 5:73–79.
20. Djukanovic, R., J. W. Wilson, K. M. Britten, S. J. Wilson, A. F. Walls, W. R. Roche, P. H. Howarth, and S. T. Holgate. 1992. Effect of an inhaled corticosteroid on airway inflammation and symptoms in asthma. *Am. Rev. Respir. Dis.* 145:669–674.
21. Rothenberg, M. E., A. D. Luster, C. M. Lilly, J. M. Drazen, and P. Leder. 1995. Constitutive and allergen-induced expression of eotaxin mRNA in the guinea pig lung. *J Exp. Med.* 181:1211–1216.
22. Post, T. W., C. R. Bozic, M. E. Rothenberg, A. D. Luster, N. Gerard, and C. Gerard. 1995. Molecular characterization of two murine eosinophil beta chemokine receptors. *J. Immunol.* 155:5299–5305.
23. Griffiths-Johnson, D. A., P. D. Collins, A. G. Rossi, P. J. Jose, and T. J. Williams. 1993. The chemokine, eotaxin, activates guinea-pig eosinophils in vitro and causes their accumulation into the lung in vivo. *Biochem. Biophys. Res. Commun.* 197:1167–1172.
24. Ponath, P. D., S. Qin, D. J. Ringler, I. Clark-Lewis, J. Wang, N. Kassam, H. Smith, X. Shi, J. -A. Gonzalo, W.

Newman, J. -C. Gutierrez-Rainos, and C. R. Mackay. 1996. Cloning of the human eosinophil chemoattractant, eotaxin. *J. Clin. Invest.* 97:604–612.
25. Bartels, J., C. Schluter, E. Richter, N. Noso, R. Kulke, E. Christophers, and J. M. Schroder. 1996. Human dermal fibroblasts express eotaxin: molecular cloning, mRNA expression, and identification of eotaxin sequence variants. *Biochem. Biophys. Res. Commun.* 225:1045–1051.
26. Neitzel, H. 1986. A routine method for the establishment of permanent growing lymphoblastoid cell lines. *Hum. Genet.* 73:320–326.
27. Sugden, B. and W. Mark. 1977. Clonal transformation of adult human leukocytes by Epstein-Barr virus. *J. Virol.* 23:503–508.
28. Beier, D. R. 1993. Single-strand conformation polymorphism (SSCP) analysis as a tool for genetic mapping. *Mamm. Genome* 4:627–631.
29. Rothenberg, M. E., A. D. Luster, and P. Leder. 1995. Murine eotaxin: an eosinophil chemoattractant inducible in endothelial cells and in interleukin 4-induced tumor suppression. *Proc. Natl. Acad. Sci. U.S.A.* 92:8960–8964.

What is claimed is:

1. A method for diagnosis of asthma comprising identifying a nucleic acid sequence exhibiting a polymorphism in an eotaxin gene, whereby that polymorphism comprises a substitution of adenine for guanine 67 base pairs following the ATG initiation codon of the gene, whereby counting is initiated at the A in that codon, and wherein asthma is thereby diagnosed.

2. A method according to claim 1 wherein the step of identifying such polymorphism comprises comparing the polymorphism in the eotaxin gene to a normal wide type eotaxin gene (SEQ ID NO:1).

3. A method according to claim 1, wherein the identifying step comprises the steps of obtaining a biological sample and testing that sample to identify a polymorphism in nucleic acid contained therein.

4. A method according to claim 1, wherein the identifying step comprises the steps of obtaining a biological sample and testing that sample to identify a variant protein therein associated with the polymorphism.

5. A method according to claim 3, wherein the identifying step comprises any of sequencing and probing the nucleic acid.

6. A method according to claim 4, comprising identifying a variant eotaxin protein in which threonine is substituted for alanine in the 23rd position.

7. A method according to claim 5, wherein the identifying step comprises the step of amplifying a nucleic acid contained in the biological sample.

8. A method according to claim 6, wherein the substitution is with respect to a wild type eotaxin protein associated with a wild type eotaxin gene (SEQ ID NO:1).

9. A method according to claim 7, wherein the amplifying step comprises the step of amplifying the nucleic acid by polymerase chain reaction (PCR).

10. A method according to claim 8, wherein the identifying step comprises the step of contacting the biological samples with immunolabelling agents.

11. A method according to claim 9, wherein the identifying step comprises the step of testing the nucleic acid by a single-strand conformation polymorphism (SSCP) technique.

12. A method according to any of claims 9 or 11, comprising the step of contacting the nucleic acid with a primer comprising any of the sequences AGAAACCACCACCTCTCACG (SEQ ID NO:2) and
GAGAATTTGCAGTGAGTCTGT (SEQ ID NO:3).

13. A method according to claim 9, wherein the identifying step comprises the step of testing the nucleic acid by an amplification refractory mutation system (ARMS) technique.

14. A method according to claim 10, wherein the identifying step comprises the step of contacting the biological sample with antibodies raised against an amino acid sequence expected to occur in the variant protein.

15. A method according to claim 13, wherein the testing step comprises the step of contacting the nucleic acid with a primer comprising any of the sequences GGGGCTTACCTGGCCCAAC (SEQ ID NO:4)
GGGGCTTACCTGGCCCAAT (SEQ ID NO:5) and
TCAAGGAAGGTTCTTAGATCG (SEQ ID NO:6).

16. A method for any of diagnosis and prediction of an inflammatory condition of respiratory tissues that is associated with tissue accumulation of eosinophils, wherein the method comprises the step of identifying a nucleic acid sequence exhibiting a polymorphism in an eotaxin gene, whereby that polymorphism comprises a substitution of adenine for guanine 67 base pairs following the ATG initiation codon of the gene, whereby counting is initiated at the A in that codon, and wherein the inflammatory condition is thereby diagnosed or predicted.

17. A method according to claim 16 comprising the step of identifying such polymorphism with respect to a normal wild type eotaxin gene (SEQ ID NO:1).

18. A method according to claim 16, wherein the identifying step testing that sample to identify a polymorphism in nucleic acid contained therein.

19. A method according to claim 16, wherein the identifying step comprises the steps of obtaining a biological sample and testing that sample to identify a variant protein therein associated with the polymorphism.

20. A method according to claim 18, wherein the identifying step comprises any of sequencing and probing the nucleic acid.

21. A method according to claim 19, comprising identifying a variant eotaxin protein in which threonine is substituted for alanine in the 23rd position.

22. A method according to claim 20, wherein the identifying step comprises the step of amplifying a nucleic acid contained in the biological sample.

23. A method according to claim 21, wherein the substitution is with respect to a wild type eotaxin protein associated with a wild type eotaxin gene (SEQ ID NO: 1).

24. A method according to claim 22, wherein the amplifying step comprises the step of amplifying the nucleic acid by polymerase chain reaction (PCR).

25. A method according to claim 23, wherein the identifying step comprises the step of contacting the biological samples with immunolabelling agents.

26. A method according to claim 24, wherein the identifying step comprises the step of testing the nucleic acid by a single-strand conformation polymorphism (SSCP) technique.

27. A method according to any of claims 24 or 26, comprising the step of contacting the nucleic acid with a primer comprising any of the sequences AGAAACCACCACCTCTCACG (SEQ ID NO: 2) and
GAGAATTTGCAGTGAGTCTGT (SEQ ID NO: 3).

28. A method according to claim 24, wherein the identifying step comprises the step of testing the nucleic acid by an amplification refractory mutation system (ARMS) technique.

29. A method according to claim 25, wherein the identifying step comprises the step of contacting the biological sample with antibodies raised against an amino acid sequence expected to occur in the variant protein.

30. A method according to claim 28, wherein the testing step comprises the step of contacting the nucleic acid with a primer comprising any of the sequences GGGGCTTACCTGGCCCAAC (SEQ ID NO: 4)
GGGGCTTACCTGGCCCAAT (SEQ ID NO: 5) and
TCAAGGAAGGTTCTTAGATCG (SEQ ID NO: 6).

* * * * *

UNITED STATES PATENT AND TRADEMARK OFFICE
CERTIFICATE OF CORRECTION

PATENT NO. : 6,548,245 B1
DATED : April 15, 2003
INVENTOR(S) : Craig M. Lilly et al.

It is certified that error appears in the above-identified patent and that said Letters Patent is hereby corrected as shown below:

Title page,
Item [75], Inventors: please delete "Andrew D. Luster; Jeffrey M. Drazen, both of Winchester," and insert therefor -- Andrew D. Luster, Wellesley; Jeffrey M. Drazen, Winchester, --

Column 1,
Line 12, delete "Basedron" and insert therefor -- Based on --.

Column 2,
Line 27, delete "MRNA" and insert therefor -- mRNA --.

Column 3,
Line 1, delete "FIGS. 2A-B depicts" and insert therefor -- FIGS. 2A and 2B depict --.
Line 59, after "(21-23)." insert therefor -- Immunohistochemical studies of inflamed and adjacent non-inflamed upper airways have --.

Column 5,
Line 23, delete the first occurrence of "C." and insert therefor -- C --.
Lines 27, 28, 29, 30, 34, 37 and 51-55, delete each instance of "C." and insert therefor -- C --.
Line 35, delete "a 4" and insert therefor -- A 4 --.
Line 44, delete "GGGCTTACCTGGCCCAAC" and insert therefor
-- GGGGCTTACCTGGCCCAAC --.
Line 45, delete "GGGGCTTACCTGQCCCAAT" and insert therefor
-- GGGGCTTACCTGGCCCAAT --.

Column 8,
Line 1, delete "Klenim" and insert therefor -- Klemm --.

Column 15,
Line 22, delete "wide" and insert therefor -- wild --.
Lines 41 and 42, delete the two instances of "wild type eotaxin" and insert therefor
-- wild type normal eotaxin --.
Line 48, delete "immunolabelling" and insert therefor -- immunolabeling --.

UNITED STATES PATENT AND TRADEMARK OFFICE
CERTIFICATE OF CORRECTION

PATENT NO. : 6,548,245 B1
DATED : April 15, 2003
INVENTOR(S) : Craig M. Lilly et al.

It is certified that error appears in the above-identified patent and that said Letters Patent is hereby corrected as shown below:

<u>Column 16,</u>
Line 29, insert after "identifying step" the following phrase -- comprises the steps of obtaining a biological sample and --.
Lines 45 and 46, delete the two instances of "wild type eotaxin" and insert therefor -- wild type normal eotaxin --.
Line 52, delete "immunolabelling" and insert therefor -- immunolabeling --.

Signed and Sealed this

Twenty-third Day of September, 2003

JAMES E. ROGAN
*Director of the United States Patent and Trademark Office*